(12) United States Patent
Roig Munill et al.

(10) Patent No.: US 11,250,943 B2
(45) Date of Patent: Feb. 15, 2022

(54) SAMPLE TRACEABILITY DEVICE AND METHOD FOR MEDICAL RESEARCH AND/OR DIAGNOSIS

(71) Applicant: EMS PATHOLOGY MEDICAL SOLUTIONS, S.L., La Garriga (ES)

(72) Inventors: Francesc Roig Munill, la Garriga (ES); Daniel Badia Pey, La Garriga (ES); Joan Xufre Neto, La Garriga (ES); Kilian Gozalbo Torne, La Garriga (ES)

(73) Assignee: EMS PATHOLOGY MEDICAL SOLUTIONS, S.L., La Garriga (ES)

( * ) Notice: Subject to any disclaimer, the term of this patent is extended or adjusted under 35 U.S.C. 154(b) by 552 days.

(21) Appl. No.: 15/512,514

(22) PCT Filed: Sep. 23, 2015

(86) PCT No.: PCT/ES2015/070692
§ 371 (c)(1),
(2) Date: Mar. 17, 2017

(87) PCT Pub. No.: WO2016/046441
PCT Pub. Date: Mar. 31, 2016

(65) Prior Publication Data
US 2017/0293719 A1    Oct. 12, 2017

(30) Foreign Application Priority Data
Sep. 26, 2014   (ES) .................. P201431423

(51) Int. Cl.
*G16H 30/20*      (2018.01)
*G06K 7/10*       (2006.01)
(Continued)

(52) U.S. Cl.
CPC ............ *G16H 30/20* (2018.01); *G01N 35/00* (2013.01); *G01N 35/00732* (2013.01);
(Continued)

(58) Field of Classification Search
CPC .. G06Q 50/22–24; G16H 30/20; G16H 10/40; G01N 35/00; G01N 35/00732;
(Continued)

(56) References Cited

U.S. PATENT DOCUMENTS 6,922,208 B2 * 7/2005 Shniberg .............. G06K 7/1095
                                                   348/169
8,944,322 B2 * 2/2015 White .................. G06K 7/1096
                                                   235/383

(Continued)

FOREIGN PATENT DOCUMENTS

WO        2013/052990 A1      4/2013

OTHER PUBLICATIONS

Nowakowski S.E. et al., "A Flexible System To Capture Sample Vials In a Storage Box—The Box Vial Scanner", Proceedings of the 31st Annual International Conference of the IEEE Engineering in Medicine and Biology Society: Engineering the Future of Biomedicine, EMBC 2009, IEEE, Sep. 3, 2009, pp. 1718-1721, XP031638658, ISBN: 978-1-4244-3296-7.

(Continued)

*Primary Examiner* — Matthew Mikels
(74) *Attorney, Agent, or Firm* — Knobbe, Martens Olson & Bear, LLP (57) ABSTRACT

Sample traceability device and method for medical research and/or diagnosis. The invention relates to a sample traceability device for medical research and/or diagnosis, comprising a one-dimensional or two-dimensional optical code, the device comprising a system for reading one-dimensional or two-dimensional optical codes and a sample tracing control device comprising a sample tracing database manager, and a user interface screen. Said traceability device also comprises: an area for depositing at least two samples, a system for illuminating the deposit area, at least one digital (Continued)

camera oriented towards said deposit area, and a device for processing the image, said image processing device comprising: a module for locating said optical codes, and a module for reading the located optical codes, the sample tracing control device automatically receiving the information generated by the module for reading the located optical codes.

12 Claims, 9 Drawing Sheets

(51) Int. Cl.
*G01N 35/00* (2006.01)
*G16H 10/40* (2018.01)
*G06K 7/14* (2006.01)

(52) U.S. Cl.
CPC .......... *G06K 7/10* (2013.01); *G06K 7/10722* (2013.01); *G06K 7/10861* (2013.01); *G06K 7/1413* (2013.01); *G06K 7/1417* (2013.01); *G06K 7/1443* (2013.01); *G06K 7/1447* (2013.01); *G16H 10/40* (2018.01); *G01N 2035/00752* (2013.01); *G01N 2035/00772* (2013.01)

(58) Field of Classification Search
CPC .......... G01N 2035/00752; G01N 2035/00772; G06K 7/10; G06K 7/10722; G06K 7/10861; G06K 7/1413; G06K 7/1417; G06K 7/1443; G06K 7/1447

See application file for complete search history.

(56) References Cited

U.S. PATENT DOCUMENTS

| | | | |
|---|---|---|---|
| 10,547,798 B2 * | 1/2020 | Douris | G06Q 30/02 |
| 2009/0110253 A1 | 4/2009 | Torre-Bueno | |
| 2009/0214088 A1 | 8/2009 | Sorenson et al. | |
| 2012/0048937 A1 * | 3/2012 | Dahari | G06K 7/14 |
| | | | 235/462.08 |
| 2012/0292392 A1 * | 11/2012 | Kim | G06Q 20/3274 |
| | | | 235/437 |
| 2013/0020392 A1 * | 1/2013 | Olmstead | G07G 1/0063 |
| | | | 235/440 |
| 2013/0306729 A1 | 11/2013 | Dilks et al. | |

OTHER PUBLICATIONS

Extended Search Report for Application No. 15844717.7, dated May 7, 2018 in 11 pages.

* cited by examiner

SAMPLE TRACEABILITY DEVICE AND METHOD FOR MEDICAL RESEARCH AND/OR DIAGNOSIS

CROSS-REFERENCE TO RELATED APPLICATIONS

This application is the U.S. National Phase under 35 U.S.C. § 371 of International Application PCT/ES2015/070692, filed Sep. 23, 2015, which claims priority to Spanish Patent Application No. P201431423, filed Sep. 26, 2014. The disclosures of the above-described applications are hereby incorporated by reference in their entirety.

FIELD OF THE INVENTION

The present invention relates to a device and a method for tracing samples in medical diagnosis and related research environments.

BACKGROUND OF THE INVENTION

In medical laboratories both for clinical analysis and anatomical pathology, haematology, etc., the IT system must incorporate a sample tracing control system.

The samples must be identified and the tracing thereof documented from the time the samples enter the laboratory for recording and classification, through the preparation and completion of the necessary analyses, up to delivery and diagnosis by the competent doctor as well as the subsequent archiving and storage thereof. A record is thus created of the passage of each sample through the various points of the laboratory circuit.

This tracing allows identification of which sample it is, which phase of the process it has reached, which user or users were involved in the process, when it was processed, where it was processed and also how long it took to pass through said process.

This sample tracing control is vital in order to guarantee total security for the patient and proper operation of laboratories, ensuring the correct circuit that each sample must follow in the laboratory. Finally, the sample tracing record allows any incidents and non-conformity events that may occur to be resolved.

At the present time, sample tracing control is carried out with the aid of optical codes, which may be one-dimensional (such as bar codes, for example) or two-dimensional (such as data matrix or QR, for example). Said optical codes are printed on adhesive labels and stuck directly on the sample containers, or printed directly on said containers. Said codes are read by readers which, in the case of the commercially available devices, are always special laser devices which translate the one-dimensional (1D) or two-dimensional (2D) graphic into a web of alphanumeric characters which are automatically entered into the computer so that said computer knows which sample it is. From this moment and using said information, the application in the IT system will react as it has been programmed to do.

The known one-dimensional or two-dimensional code reading devices are only capable of completing the read/write process for a single code each time, so that said process must be repeated as many times as there are codes to be read. The time of a read/write operation for an average user varies between one and three seconds.

The present system of individual laser readers leads to a productivity problem in laboratories, especially at the points where batches of samples are processed, and it is therefore necessary to read a great many samples. This means that present readers are real bottlenecks in the circuit owing to the limitation of being a manual task carried out individually for each sample. When said process has to be carried out mechanically for a large quantity of samples, a significant investment of time is required. Unfortunately, in some cases the end result is a failure to take the trace at said point, with all the losses that entails.

Furthermore, the validation systems currently used often produce the "read skipped" error when the operator takes a sample as read, when in reality the reader has recognised the sample preceding or following the one that was not read. Although it can be mitigated by double-reading alarms in IT applications, this can continue to cause errors and is a source of low productivity since, once the error has occurred, it is difficult to locate where it occurred. If the code of a sample has not been read correctly, it is very difficult to locate which code was misread.

The known systems limit the possibility of IT applications being able to act by displaying information to the user about the entire batch instantaneously or 'on the fly'. This makes it impossible to use IT platforms to support the user during important operations such as verifying batches of samples for a case or study, or verifying batches to be sent to the next process, whether this is the next machine or the next professional involved (such as the pathologist designated to diagnose said samples, for example) or selecting from among all the samples in the batch those which are urgent in order to prioritise them in the process, etc.

Document US2009110253A1 discloses an error prevention system in the identification of biological samples on slides, in which a single slide with a code is placed under a camera, the camera takes the image, while a special label reader reads the label or code on the sample. Next the system compares the form of the biological sample with an earlier image of the same sample and compares the form of the biological sample in both images. This document does not disclose a traceability control system, the reading being carried out only one sample at a time and with the object of comparing the image of the sample with an image taken earlier in order to discount an error in labelling or identifying the sample.

US 20130306729 A1 discloses a device for reading bar codes stuck to test tubes in an array-type test tube rack. The device consists of a box with a window through which various cameras take readings. Inside the box are various lights and the window has a filter. The box also comprises opaque elements for blocking the light and four cameras. The images are processed by the internal controller of the device in order to extract the codes, which is the output offered by the device as information.

It does not disclose or suggest technical means that would allow the operator to work by batches (to validate by batch, check errors by batch, etc.).

US 2012048937 A1 discloses a bar code reader of which the physical terminal is a hand-held device which is capable of reading a plurality of bar codes in batch form simultaneously.

Unlike US 20129048937, this document discloses the existence of a screen, a storage unit and a bar code detection module. Reading is carried out in batches and there is a batch generator module. However, this document does not disclose means that allow the operator to work in batches. Rather, it states that the bar code selection module is configured to select a single bar code from among a plurality of bar codes. The output of the device is limited to information on the bar codes captured in the image, in order to be displayed by the interface screen. Although detection is carried out in batches, each code is processed separately.

An object of the present invention is to disclose a device and a method which overcome the above-mentioned drawbacks.

SUMMARY OF THE INVENTION

The present invention discloses a system that allows transition from individual validation to batch validation, which provides a solution to the drawbacks of the prior art. The present invention discloses preparing a reading zone which contains various samples, allowing an image taken using a camera (preferably a digital camera) to be processed later, which allows the user/operator to validate the passage of said batches through that work point and in addition to interact extremely flexibly with the information associated with said batches in the database.

More particularly, the present invention discloses a device and a method which can be used in sample processing processes and which can identify, read and transcribe to the computer multiple one-dimensional or two-dimensional codes simultaneously and rapidly.

Still more particularly, the present invention discloses a sample traceability device for medical diagnosis and/or research, a one-dimensional or two-dimensional optical code, the device comprising a one-dimensional or two-dimensional code reader and a sample tracing control device which comprises a sample tracing database manager, and a user interface which comprises an interface screen, the device comprising:

a zone for placing at least two samples;

preferably, a system for illuminating the placing zone, if necessary;

at least one digital camera oriented towards said placing zone;

an image-processing device, which comprises:

i. a module for locating said optical codes;

ii. a module for reading the located optical codes;

an automatic device for sending the information generated by the reading module to the database manager and in that the screen is configured to be able to display both the image captured and the information coming from the database manager, the control device for this purpose being configured to display on the interface screen the image taken by the at least one digital camera, and information relating to the samples, identified by means of the optical codes located by the locating module and in that the control device is configured to be able to generate a multiple order to said database manager relating to some or all the optical codes located by the locating module and read by said reading module.

The present invention overcomes the productivity problem in sample validation and traceability operations carried out by the operator or technician by extracting from the code reader not only the codes, but also the image of the samples and the use both of said data and of the images in the interface. This allows the technician to carry out operations by batches and not by samples.

In the present invention, optical code should be understood as any type of identifier that can be identified optically.

In a particular embodiment, the placing zone of at least two samples, the system for illuminating the placing zone and said at least one digital camera are arranged in a single body or casing.

Preferably, said body or casing comprises a tower or mast at the upper end of which the system for illuminating the placing zone and said at least one camera are arranged.

More preferably, the receiving zone should be suitable for the sample containers to leave all the optical codes exposed to the camera or cameras, and said zone may therefore be a tray, for example a tray for planar containers or other supports specific to another type of container.

More preferably, the control device is configured to mark the optical codes located by the locating module on the image taken by said digital camera.

The present invention also discloses a method that allows mass validation, that is, verification of passing through a trace monitoring point, as understood in the prior art, with the difference that the present invention makes it possible to do this for multiple codes simultaneously. This functionality allows 100 codes, for example, to be validated in a time of approximately one second, whereas the same validation using the conventional method would take from 100 to 300 seconds, which represents a more than one hundred-fold reduction in time. With this novel solution, the low productivity of the traditional method using individual laser readers mentioned above is greatly improved.

More particularly, the present invention also discloses a method for tracing samples in hospital environments, the method comprising the steps of:

placing a one-dimensional or two-dimensional optical code on the samples to be traced;

reading said optical code on said samples by means of an optical code reader;

managing a sample database by means of a sample tracing control device which comprises a database manager and a user interface screen, in which the step of reading the sample by means of an optical code reader comprises the following steps:

placing at least two samples in a sample receiving zone;

preferably, illuminating the sample receiving zone;

taking an image of the sample receiving zone using at least one digital camera;

processing the image taken, said processing comprising:

i. automatically locating optical codes by means of a locating module;

ii. automatically reading the codes located by the locating module by means of a reading module;

sending the information generated by the read module to the database manager by automatic means and in that the interface screen displays the image taken and/or information from the database manager and in that it comprises generating a multiple order to said database manager relating to some or all of the optical codes located in said location and in that it comprises the step of displaying on the screen the image taken at a user interface.

The present invention advantageously allows for generation of a multiple order to said database manager relating to some or all of the optical codes located in said location, which allows the user to work in batches (validation, checking of errors or of intrusive elements in the batch, etc.).

Preferably, the method also comprises the step of displaying the image taken at a user interface.

Yet more preferably, the method comprises a step of adding information relating to the located optical codes to the image displayed at the user interface.

Still more preferably, the control device marks the location of the optical modules located by the locator on the image taken by said at least one digital camera and displayed at the user interface.

Other advantages of the present invention arise due to the synergistic effect between the validation system of the present invention and the user interface. The present invention can continuously provide images and/or information about the set of codes in the field of vision of the camera or cameras. With this information, the control device can display to the user on a screen all the information available in the database for those samples. The information to be displayed and the way it is displayed can be configured according to the needs of the user or the work point. This functionality allows the user, simply by placing a tray with a batch of samples in the viewing zone, to solve tasks or issues such as, for example, checking if the device has detected and read all the samples. To do this, the user interface screen can display the image captured by the camera with all the samples and their bar codes highlighting unequivocally the codes identified. The possibility of the operator allowing a sample to pass unread is thus eliminated. It is also easier to check if all the samples are assigned to the correct route, for example, if they are going to the right pathologist. In addition, it is possible to check easily using the images taken and the user interface screen if all the samples correspond to a case study or patient. Moreover, it is possible to discriminate with ease which samples should take one route and which should take another (for example, because they are different sample types).

In the present application, 'sample' is understood to be both the unit formed by the biological sample and the element that holds said sample, or sample holder.

BRIEF DESCRIPTION OF THE DRAWINGS

To aid understanding, explanatory yet non-limiting drawings are included of an embodiment of the sample traceability device and method for medical diagnosis and/or research according to the present invention.

DETAILED DESCRIPTION OF THE PREFERRED EMBODIMENTS

FIGS. 1 to 4 show a possible embodiment according to the present invention which comprises one or more digital cameras -5- which, for example, may comprise an electronic image sensor (such as CCD or CMOS, for example), a system of lenses which constitutes the optics and an internal electronic system of the camera.

The embodiment shown also comprises a zone -2- for placing or receiving the samples -100- with the one-dimensional or two-dimensional codes -101- thereof. In this case, said optical codes may be, for example, bar, data matrix or QR codes. The placing zone -2- coincides with the viewing zone of the camera -5-. In the case shown in FIGS. 1 to 4, the sample -100- comprises a slide which will hold a biological sample (not shown) and a code stuck to the upper surface thereof.

The elements described are comprised in a single casing or body -1-. The casing -1- provides rigidity so as to prevent vibrations in the images taken by the camera or cameras -5-.

In particular, the body -1- shown in the figures has a base which houses a tray which coincides with the receiving zone -2- for the samples -100-, a tower or mast -3- and a head -4- which houses the camera or cameras -5- and an illumination lamp or lamps -6- which ensure suitable illumination in the placing zone -2- for the subsequent image processing.

Although not shown in the figures, the casing -1- may also comprise a power supply system for the illumination and the camera or cameras, if required (not shown in the figures).

Figure 1:
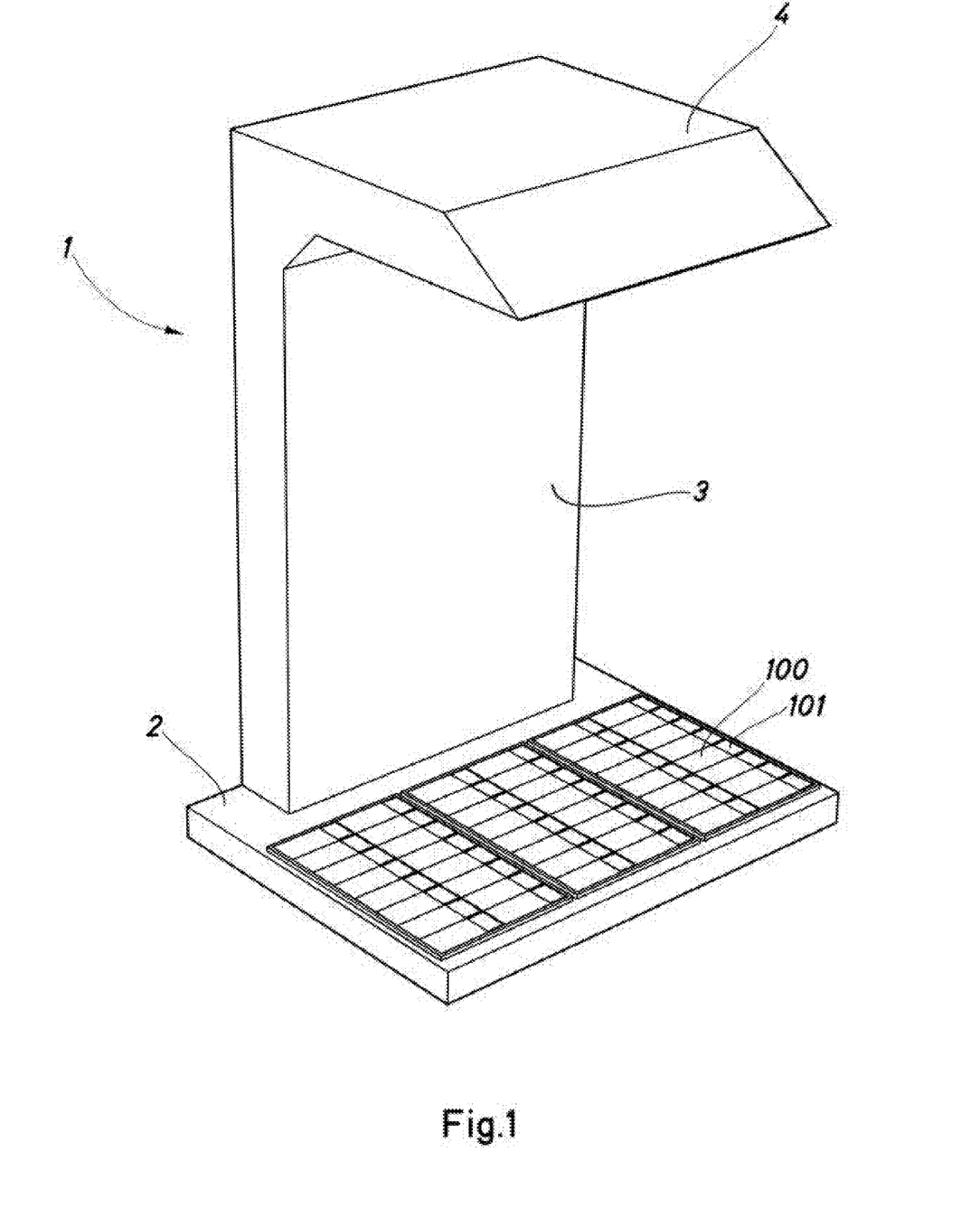
FIG. 1 is a perspective view of a device according to the present invention, in particular of a single casing or body which comprises a sample receiving zone, an image capture system and a lighting system.
Figure 2:
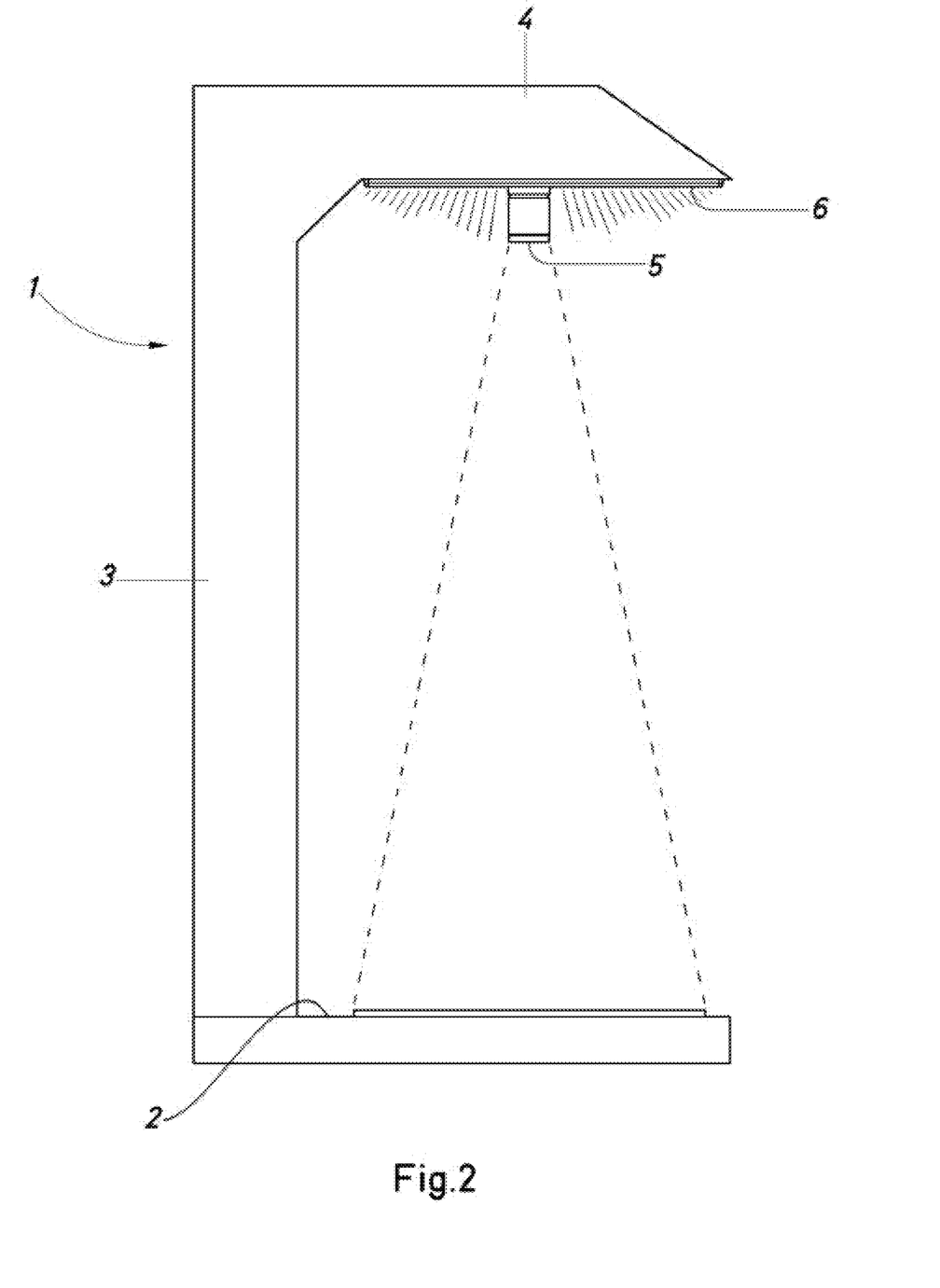
FIG. 2 is a view in side elevation of the device of FIG. 1.
Figure 3:
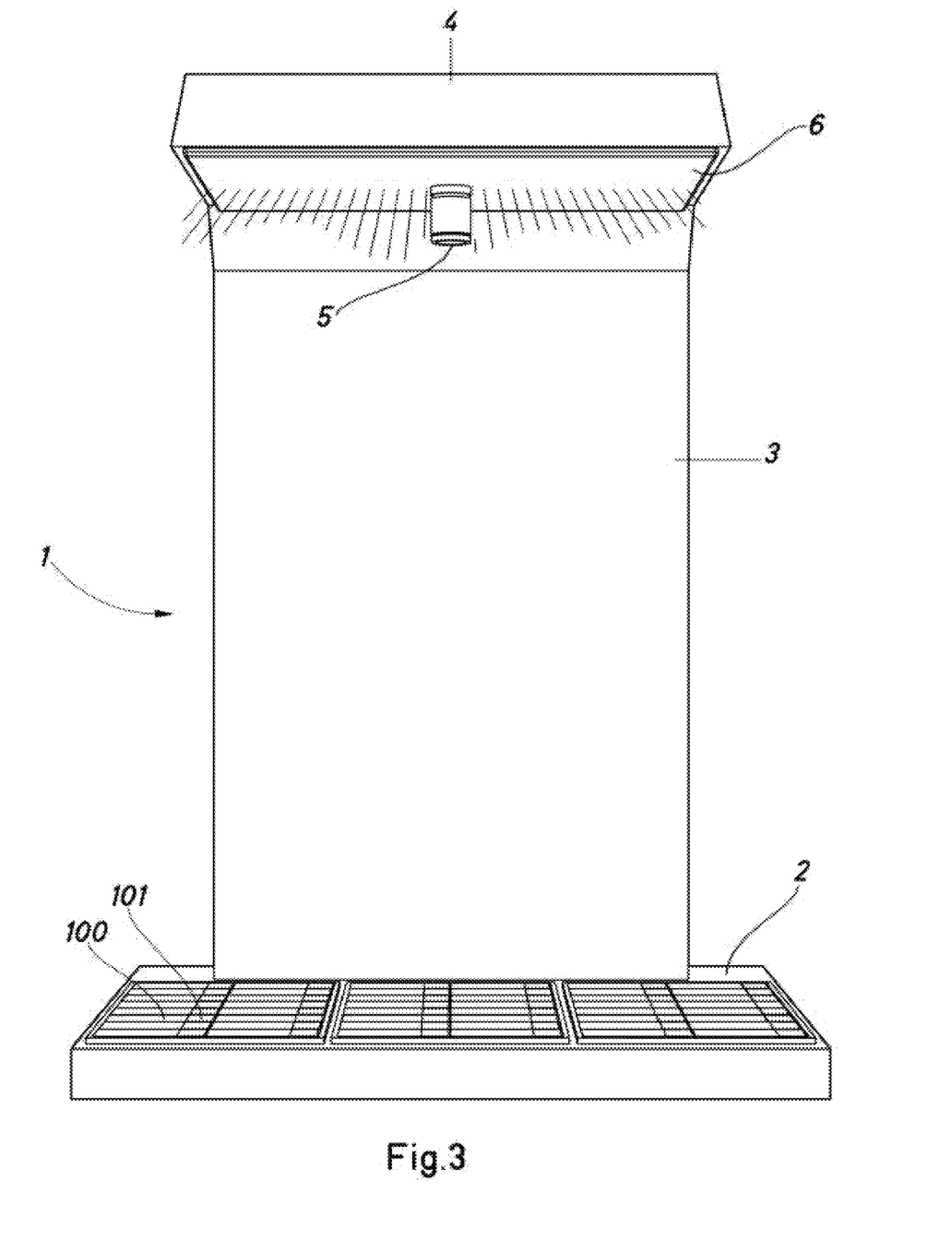
FIG. 3 is another perspective view of the device of FIG. 1.
Figure 4:
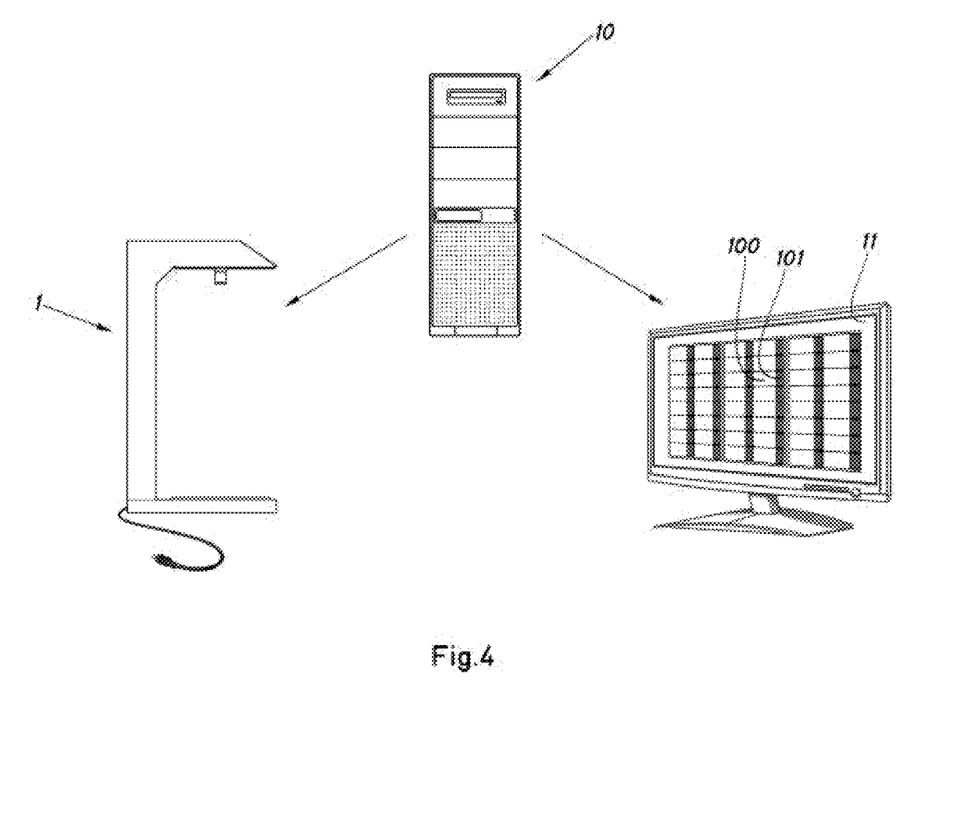
FIG. 4 is a schematic view of the device of FIGS. 1 to 3 connected to an electronic control device and to a user interface screen.

As can be seen in FIG. 4, the embodiment shown also comprises a computer -10- configured as a control device, to which the camera -5- is connected and which collects the images generated by the camera -5-, and using one or more modules it is capable of identifying, decoding and transcribing the information contained in the codes -101- which appear in the image.

The embodiment also comprises a user interface which in turn comprises a screen -11- where the image viewed by the camera is shown with the samples -100- having a recognised code. The code can also be shown on the screen -11- or alternatively the space -102- for the code in the image can be used to display information about the sample. The different validation and information options relevant to the user can also be displayed on the screen -11-.

Figure 5:
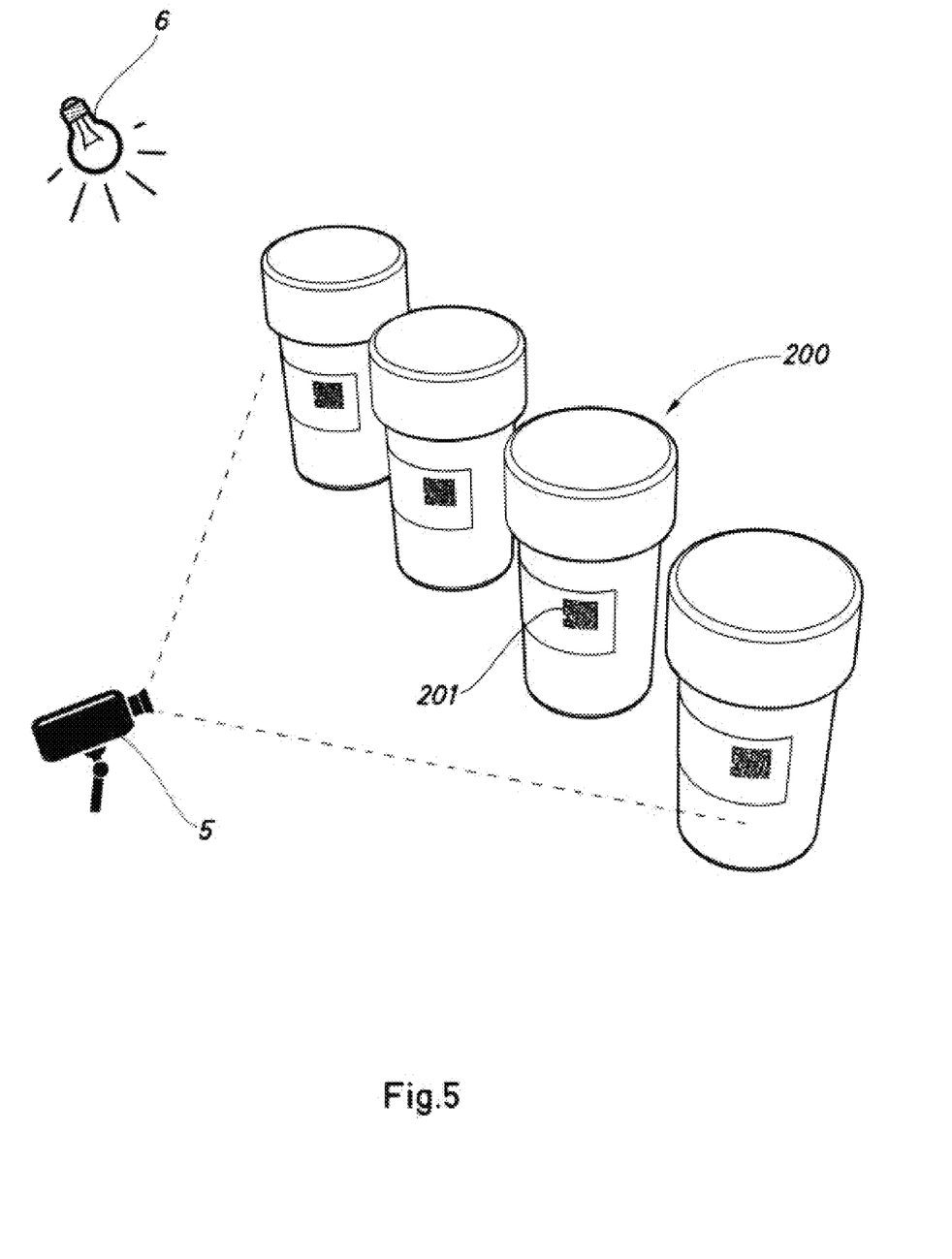
FIG. 5 is a schematic view of a variant of that of FIG. 1, for another sample type.

FIG. 5 is a schematic view of another particular embodiment of some elements incorporated in the present invention. In particular, the embodiment shown is intended for container-type samples -200- which contain the biological sample inside. A two-dimensional code -201- has been stuck to the outside of the container. In the embodiment shown, it is possible to dispense with grouping together the receiving/placing zone, camera and illumination in the same body, it being possible to place a camera or cameras -5- in an arrangement suitable for reading codes -201- and one or more illumination lamps -6- can be placed in order to prevent there being areas of shadow which would prevent a correct reading of the codes.

Figure 6:
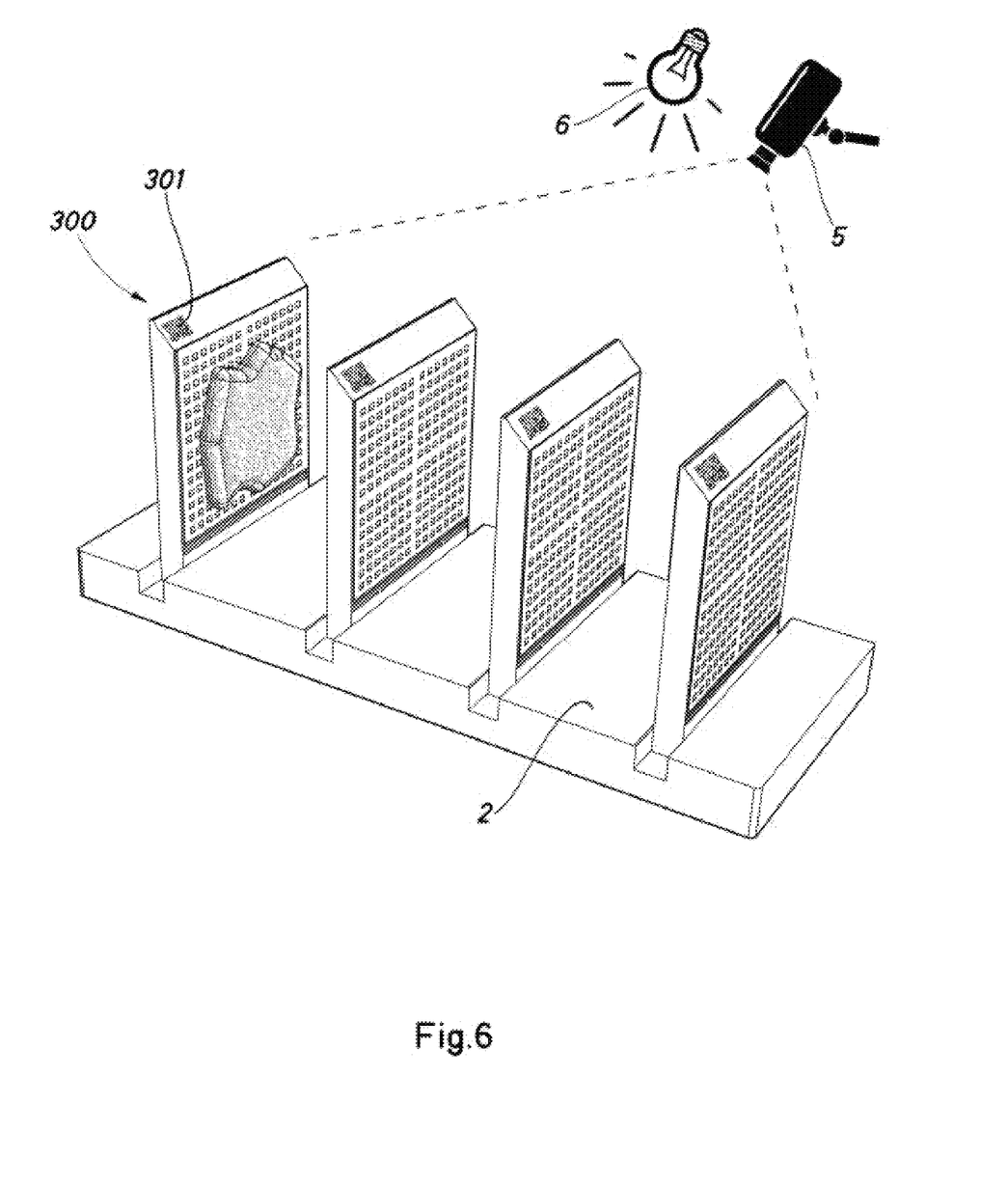
FIG. 6 is a schematic view of another variant of that of FIG. 1, for yet another sample type.

FIG. 6 shows yet another variant, relating to samples -300-, where the sample holder is of the cassette type. In this case, a two-dimensional code -301- can be stuck, etched or printed directly on the upper portion of the cassette, as can be seen in the figures.

As can also be seen in the figures, in this case, the camera -5- and the illumination lamp -6- should be placed in a specific way relative to the receiving/placing zone -2-, owing to the particular morphology of the sample holder.

Figure 7:
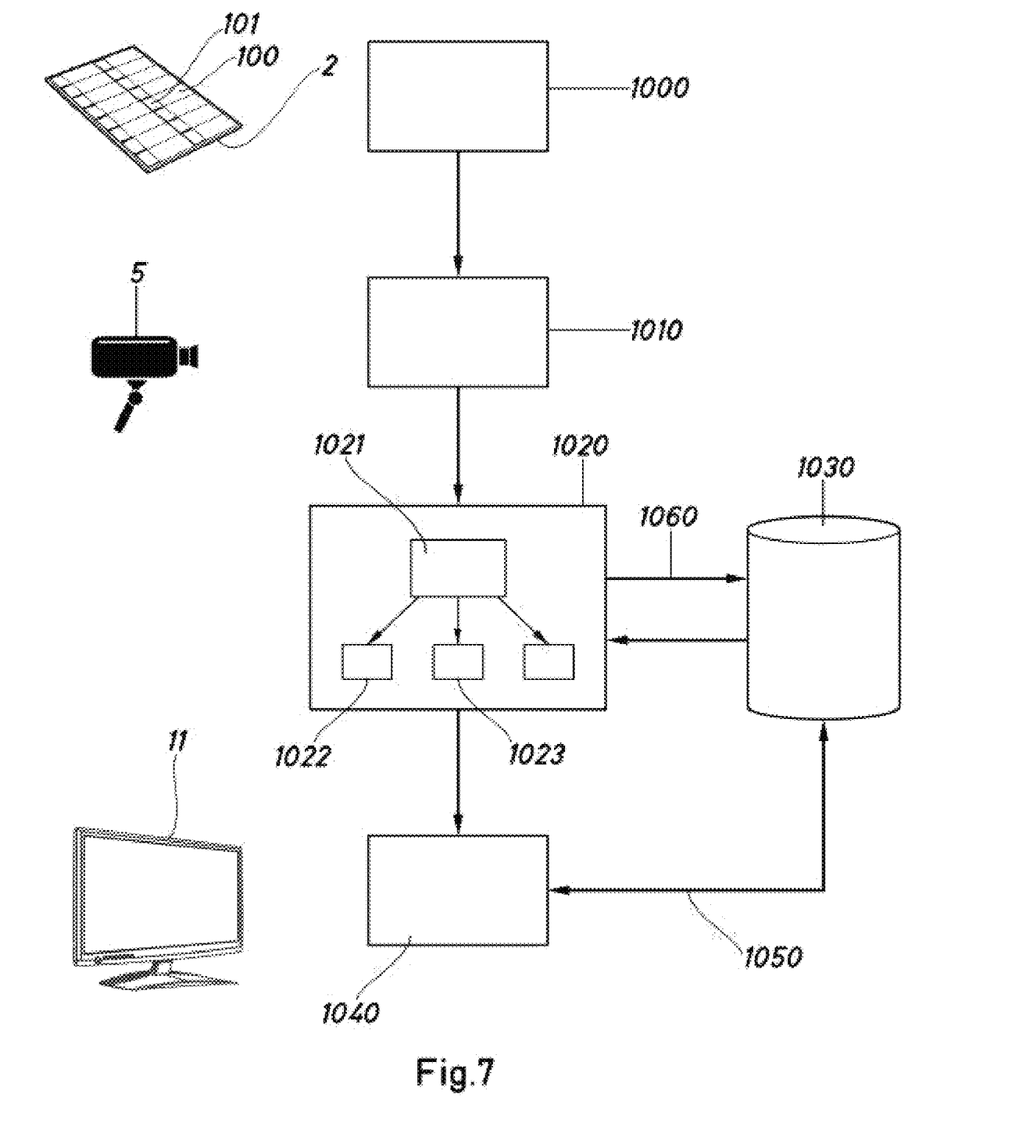
FIG. 7 is a block diagram of the method according to the present invention.

As shown in FIG. 7, the system operating sequence, in a preferred embodiment, is as follows:

placing -1000- the samples -100- having a code -101- in the placing zone -2-.

capturing -1010- the image: the camera -5- constantly captures images of the sample verification zone.

processing -1020- the image: a locating module -1021-, for example executed by a computer, scans the image taken by the camera -5- in search of one-dimensional and two-dimensional codes -101-, and a reading module interprets -1022-, -1023- and translates said codes into numbers and letters.

searching -1060- the database -1030-: the control device searches the database -1030- of the laboratory management system for stored information relating to those samples. The database -1030- may allow the extraction of information on, for example, the case or study to which said samples relate, the pathologist to whom they are assigned, how urgent they are, how much time has passed since said samples were received, etc.

presenting -1040- on screen -11-: an interface module displays on screen all the information considered relevant for the user, such as the image captured by the camera -5- with the samples -100-, for example.

At the command of the user, details can be shown about the samples individually, such as whether the sample has been validated or if the sample should already have been processed, or if the sample relates to an urgent case, etc. In general, the control device will be able to display on screen all the information available in the database about said sample.

At the command of the user, details can be produced about the batches of samples, such as whether said batch is homogenous as regards its destination either to a subsequent phase of the process or to a particular operator, etc. (it can show everything available in the database on said sample and on the process environment known by the laboratory management system).

Modifying -1050- the database -1030-: the control device, at the request of the system operator, modifies the status of the sample. For example, if the sample or samples have already left the laboratory or have already been sent or received. Modifications can be made individually or by batch, such as, for example, to all the samples collected in a particular image, or a sub-group thereof.

Figure 8:
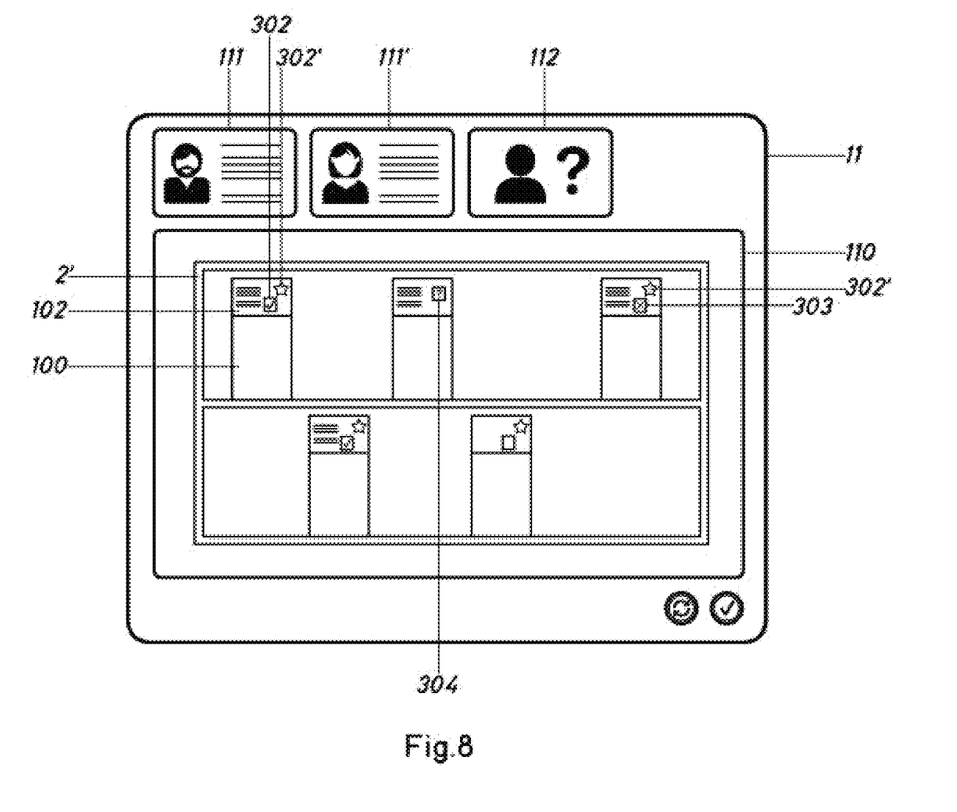
FIG. 8 shows an example of the interface screen display according to the present invention.

FIG. 8 shows an example of a display on the screen -11-. The screen has an image zone -110- in which the image captured by the camera of a receiving zone -2'- is displayed. In the present case, the receiving zone is a distribution tray which comprises a series of samples -100-. One of the tasks of the technician consists of distributing each of the samples/trays to the assigned/appropriate pathologist. To do this, it is important to be able to discern whether all the object holders with the samples in a tray belong to the intended recipient or not. To do this, the control device has superimposed visual indicators on the space where the optical code is positioned (in this case buttons -302-, -303-, -304- and asterisks -302'-). By clicking on the buttons, the information relating to the sample is displayed. Each button also provides the technician with relevant visual information. Thus, the button -302- with a 'double check' indicates to the technician that those samples are ready to be validated and on validation complete the case or study. The button -303- indicates with an X that that sample has not passed through the previous phases and therefore should not yet be present in this phase of the analytical process. The button -113- with a question mark indicates that this sample does not relate to any reference in the database -1030- and that the management system therefore has no record of it. Simply positioning the tray in the field of vision of the camera -5- allows rapid identification of whether all the object holders with samples in a tray belong to the same intended recipient, without the need to carry out costly checks sample by sample. The arrangement shown on screen also allows all the samples to be selected and assigned to a pathologist using a single click. Assignment by batch is therefore possible.

Figure 9:
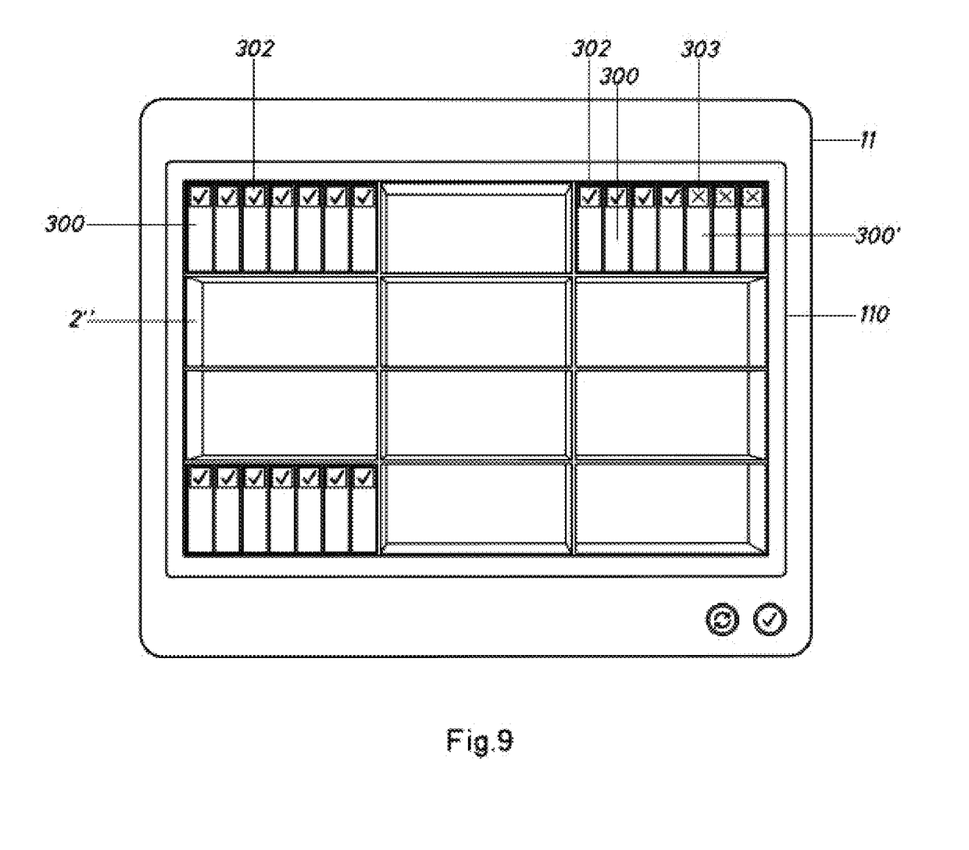
FIG. 9 shows a second example of the interface screen display according to the present invention.

FIG. 9 shows another example of a display of an image shown by the interface screen-11-. In this case, a rack -2"- of blocks or cassettes -300- can be seen in the image zone -110- which in this case are waiting to enter the tissue processor. In this case, the system helps the technician detect blocks that are not ready to enter the process machine or that have incorrect information. To do this, the control device superimposes indicator buttons -302- having a 'checked' (✓) indicator on the optical code of the blocks -300- if, according to the information available in the database -1030-, the sample is ready to be processed. If it is not, or if there is erroneous information, as is the case in the block -300'-, the device superimposes a button -303- having the symbol 'X', giving a visual indication that the sample is not ready for processing. Thus, the technician or user can quickly become aware of the existence of samples that are not ready, their exact location, and can also know whether sets or batches can go to processing and which should be investigated or pre-processed. Moreover, simply by placing the rack 2" in the viewing zone of the camera 5 and clicking on the screen once can the entry of the samples into the tissue processor be verified, and the same operation allows their exit to be verified once the samples have been processed. This provides a level of sample tracing that has never been obtained until now with the current technology.

The present invention, by using a device not just to locate and read codes, but also to extract said image, allows mass sample validation and has advantages such as:

mass control of the entry and exit of samples into and out of the machines present in the diagnostic process; for example, tissue processors, staining machines, immunostaining machines, heat treatment machines, centrifuges, etc.

mass control of the entry and exit of samples into and out of the archives; for example, archives of containers, cassettes, paraffin blocks, object holders, Eppendorf tubes, swabs, etc.

mass step verification controls; for example, control of samples that arrive from one centre at another.

mass validation controls of the status of samples; for example, cassettes are included, object holders are already dyed/stained, paraffin blocks are cut, tubes are ready to be archived, etc.

Although the invention has been described with respect to preferred embodiments, said embodiments should not be considered as limiting the invention, which will be defined by the widest interpretation of the following claims.

What is claimed is:

1. A sample traceability device for medical diagnosis and/or research involving a one-dimensional or two-dimensional optical code, the device comprising:
    a one-dimensional or two-dimensional code reading system, and
    a sample tracing control device which comprises:
        a sample tracing database manager;
        a user interface which comprises a screen;
        a zone for placing at least two samples;
        at least one digital camera oriented towards said placing zone;
        a casing housing the at least one digital camera;
        an image-processing device, which comprises:
            i. a module for automatically locating said optical codes in an image captured by said digital camera;
            ii. a module for automatically reading the located optical codes;
        an automatic device for sending the information generated by the reading module to the database manager wherein the screen is configured to be able to display both the image captured and the information coming from the database manager, the control device for this purpose being configured to display on the interface screen the image taken by the at least one digital camera, and information relating to the samples, identified by means of the optical codes located by the locating module, the control device is configured to be able to generate a multiple order to said database manager relating to some or all of the optical codes located by the locating module and read by said reading module, the control device is further configured to be able to superimpose visual indicators on a space where the optical codes are positioned to indicate a status of the samples based on the information coming from the database manager, the casing defines the zone for placing at least two samples, said zone for placing at least two samples being rigidly connected to the at least one digital camera, and the zone for placing at least two samples coincides with a viewing zone of the at least one digital camera.

2. The device according to claim 1, wherein the control device is configured to mark the optical codes located by the locating module on the image taken by said digital camera.

3. The device according claim 1, wherein it comprises a system for illuminating the placing zone.

4. The device according to claim 3, wherein the placing zone of at least two samples, the system for illuminating the placing zone and said at least one digital camera are arranged in a single body or the casing.

5. The device according to claim 4, wherein said body or casing comprises a tower or mast at the upper end of which the system for illuminating the placing zone and said at least one camera are arranged.

6. The device according to claim 1, wherein the zone for receiving at least two samples is a tray.

7. A method of tracing samples in hospital environments, the method comprising the steps of:
  placing a one-dimensional or two-dimensional optical code on the samples to be traced;
  reading said sample by means of an optical code reader;
  managing a sample database by means of a sample tracing control device which comprises a database manager and a user interface having an interface screen,
  wherein the step of reading by means of an optical code reader further comprises the following steps:
  placing at least two samples in a sample receiving zone;
  taking an image of the sample receiving zone using at least one digital camera;
  processing the image taken, said processing comprising:
    i. automatically locating the optical codes in the image taken by means of a locating module;
    ii. automatically reading the codes located by the locating module by means of a reading module;
  sending the information generated by the reading module to the database manager by automatic means;
  displaying the image taken and/or information from the database manager on the interface screen display, and
  generating a multiple order to said database manager relating to some or all of the optical codes located in said location and displaying on the screen the image taken at a user interface, and
  superimposing visual indicators on a space where the optical codes are positioned to indicate a status of the samples based on the information coming from the database manager,
  wherein the sample tracing control device further comprises a casing which houses at least one digital camera and defines the sample receiving zone, said zone for placing at least two samples is rigidly connected to the at least one digital camera, and
  the sample receiving zone coincides with a viewing zone of the at least one digital camera.

8. The method according to claim 7 further comprising a step of adding information relating to the located optical codes to the image displayed at the user interface.

9. The method according to claim 8, wherein the control device marks the location of the located optical codes by the locating module on the image taken by said at least one digital camera and displayed at the user interface.

10. The method according to claim 7, further comprising illuminating the sample receiving zone before taking the image.

11. The device according to claim 1, wherein:
  said multiple order is to modify a database, including a modification of sample status, and
  said modifications are made by batch.

12. The device according to claim 7, wherein:
  said multiple order is to modify a database, including a modification of sample status, and
  said modifications are made by batch.

* * * * *